(12) United States Patent
Arakawa

(10) Patent No.: US 6,320,930 B1
(45) Date of Patent: Nov. 20, 2001

(54) RADIATION TOMOGRAPHY METHOD AND APPARATUS

(75) Inventor: Satoshi Arakawa, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/472,440

(22) Filed: Dec. 27, 1999

(30) Foreign Application Priority Data

Dec. 25, 1998 (JP) .................................................. 10-370892

(51) Int. Cl.⁷ .................................................... G01N 23/00
(52) U.S. Cl. ......................................................... 378/8; 378/4
(58) Field of Search .............................. 378/8, 4, 15, 21, 378/85, 146, 65

(56) References Cited

U.S. PATENT DOCUMENTS

| 5,612,985 | * | 3/1997 | Toki et al. ................................. 378/4 |
| 5,832,051 | * | 11/1998 | Lutz ........................................ 378/8 |
| 5,848,114 | | 12/1998 | Kawai et al. ............................ 378/4 |
| 5,978,439 | * | 11/1999 | Koppe et al. ............................ 378/8 |
| 5,999,587 | * | 12/1999 | Ning et al. ............................... 378/4 |
| 6,243,439 | * | 6/2001 | Arai et al. ............................... 378/20 |

FOREIGN PATENT DOCUMENTS 9-253079   9/1997   (JP) .................................. A61B/6/03

* cited by examiner

Primary Examiner—David V. Bruce
Assistant Examiner—Irakli Kiknadze
(74) Attorney, Agent, or Firm—Sughrue, Mion, Zinn, Macpeak & Seas, PLLC

(57) ABSTRACT

A radiation tomography for photographing a radiation projected image of a subject by relatively rotating a radiation source which emits a conical radiation beam and a detector which detects the conical radiation beam transmitted through the subject, with respect to the subject. The radiation tomography apparatus includes a detection unit which detects a periodic motion of a part of the subject to be photographed and a controller which controls the radiation source so that in synchronism with the detection, a timing of emitting the cone radiation beam is synchronized with constant timing at which the detected part moves.

10 Claims, 1 Drawing Sheet

RADIATION TOMOGRAPHY METHOD AND APPARATUS

BACKGROUND OF THE INVENTION

1. Field of the Invention

This invention relates generally to a method and an apparatus for radiation computed tomography employing a conical radiation beam, and more particularly to improvements in radiation tomography for photographing a moving part of a subject.

2. Description of the Related Art

Radiation tomography for a living organism such as a human body is known and uses a conical radiation (X-ray) beam emitted from a source of radiation. As an example, an X-ray tomograph that collects projection data over the entire circumference of the heart is disclosed in Japanese Unexamined Patent Publication No. 9(1997)-253079. In the X-ray tomograph, the projection data are recorded in synchronization with heartbeats by an electrocardiograph. Because the obtained projection data are not photographed when the states of the heart are all the same, only data for cases where position of the cardiac vein is considered to be the same are sampled and reconstituted.

In the aforementioned conventional example, all projection data are sampled and then only projection data for cases where the position of the cardiac vein is considered to be the same are sampled, so it will take time to sample data and it will be a waste of time. In addition, the influence of radiation on a living organism becomes greater with the lapse of time.

Furthermore, no problem will occur in photographing a part of a living organism that does not move, but there are cases where in photographing a part (such as a heart) that moves periodically, an object to be photographed moves while being irradiated with radiation. When the motion is small, it does not matter. When the motion is large, however, the outline of the image will become obscured, and consequently, there is a problem that a tomogram and a three-dimensional image of high resolution cannot be obtained.

SUMMARY OF THE INVENTION

The present invention has been made in view of the aforementioned drawbacks. Accordingly, it is an object of the present invention to provide a method and an apparatus for radiation tomography which are capable of efficiently sampling data, shortening photographing time, and reducing the influence of radiation on a living organism. Another object of the present invention is to provide radiation tomography which is capable of photographing a part of a subject that moves periodically, without obscuring the outline of the tomogram of the moving part.

To achieve the aforementioned objects and in accordance with one aspect of the present invention, there is provided radiation tomography for photographing a radiation projected image of a subject by relatively rotating a radiation source which emits a conical radiation beam and a detector which detects the cone radiation beam transmitted through the subject, with respect to the subject. The radiation tomography comprises the steps of: detecting a periodic motion of a part of the subject to be photographed; and controlling the radiation source so that in synchronism with the detection, a timing of emitting the conical radiation beam is synchronized with constant timing at which the detected part moves.

In this way, the periodic motion of a moving part of the subject that is photographed is detected and the radiation source is controlled so that in synchronism with the detection, a timing of emitting the cone radiation beam is synchronized with constant timing at which the detected part moves. Therefore, only a specific position on a subject, where image data is desired, can be photographed. As a result, data can be sampled efficiently in a short time and the influence of radiation on a living organism can be reduced.

In accordance with another aspect of the present invention, there is provided a radiation tomography apparatus for photographing a radiation projected image of a subject by relatively rotating a radiation source which emits a conical radiation beam and a detector which detects the conical radiation beam transmitted through the subject, with respect to the subject. The radiation tomography apparatus comprises detection means which detects a periodic motion of a part of the subject to be photographed and control means which controls the radiation source so that in synchronism with the detection, a timing of emitting the conical radiation beam is synchronized with constant timing at which the detected part moves.

In this way, the control means can control the radiation source so that in synchronism with the detection, a timing of emitting the cone radiation beam is synchronized with constant timing at which the detected part moves. Therefore, only a specific position on a subject, where image data is desired, can be photographed. As a result, data can be sampled efficiently in a short time and the influence of radiation on a living organism can be reduced.

A part of the subject that is photographed by the radiation tomograph is, for example, the heart of a living organism, and in that case, the constant timing at which the part moves may be the dilation period of the heart. In the case of the dilation period of the heart, the motion of the heart is least over a comparatively longer period and therefore a tomogram and a three-dimensional image of high resolution are obtained without obscuring the outline of the tomogram.

The above and many other objects, features and advantages of the present invention will become manifest to those skilled in the art upon making reference to the following detailed description and accompanying drawings in which a preferred embodiment incorporating the principle of the present invention is shown by way of illustrative example.

DESCRIPTION OF THE PREFERRED EMBODIMENTS

Figure 1:
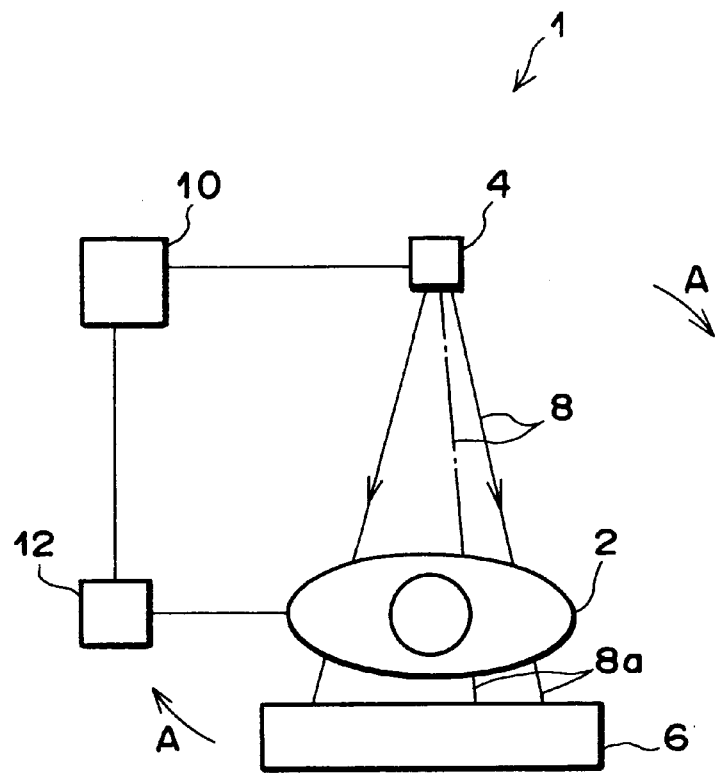
FIG. 1 is a block diagram of a radiation tomography apparatus according to an embodiment of the present invention.

Referring to FIG. 1, there is shown a preferred embodiment of a radiation tomograph 1 in accordance with the present invention. The radiation tomograph 1 includes a subject 2, a radiation source (hereinafter referred to as a ray source) 4 disposed above the subject 2, and a detector 6 disposed below the subject 2. The detector 6 employs an image intensifier, an X-ray vidicon, a combination of a fluorescent substance ($Gd_2O_2S$, Tb, CsI, Tl, etc.) and a-SiTFT, a combination of an X-ray conductor (CZT, a-Se, or $PbI_2$) and a TFT, or the like. The ray source 4 emits X rays (radiation) 8 to the subject 2. The emitted X rays 8 are transmitted through the subject 2, and the transmitted rays 8a are incident on the detector 6. The ray source 4 and the detector 6 are disposed opposite to each other and rotate around the subject 2 in the same direction indicated by an arrow A, while keeping the same position relatively. Alternatively, the subject 2 may be photographed while being rotated.

The transmitted rays 8*a* carry radiation image information about the subject 2, and in the detector 6, the radiation image information is converted to image signals representing a radiation image. After the image signals have been accumulated in image memory (not shown), they are transmitted to an external image processor, in which the image signals are reconstituted into a visible fault image or a three-dimensional image. The reconstitution is performed by a known algorithm such as a Feldkamp method (Feldkamp L A, Davis L C, Kress J W, Practical cone-beam algorithm, J Opt Soc Am A 1984:1:612–619).

A heartbeat measuring unit (hereinafter referred to simply as a measuring unit) 12, such as an electrocardiograph, a pulsometer and the like, is attached as detection means to the subject 2 through electrodes, and the heartbeat of the heart (not shown) is measured. The measuring unit 12 is electrically connected to a ray-source controller (hereinafter referred to as simply a controller) 10 which controls the ray source 4. As a result, the controller 10 operates in synchronization with heartbeats.

Figure 2:
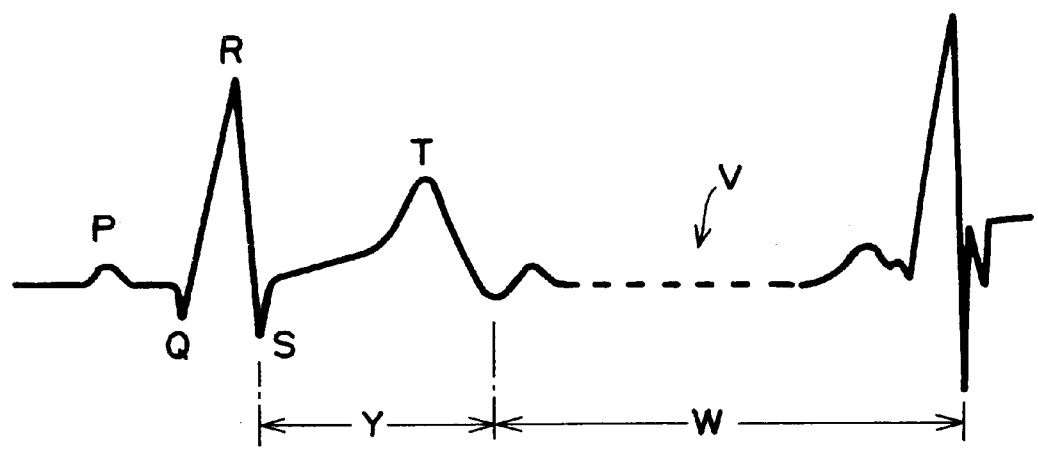
FIG. 2 is an electrocardiogram measured by a measuring unit.

FIG. 2 illustrates an electrocardiogram example of the subject 2 measured by the measuring unit 12. In the electrocardiogram, the vertical direction represents an action potential and the horizontal direction represents a temporal change. A P wave is generated when the atrium contracts and a QRS wave is generated when the ventricle contracts. A T wave is a waveform that is generated when the ventricle contracts. Thereafter, a substantially constant waveform V continues. This waveform V represents the dilation period W of the ventricle. The waveform V that has the least change and the longest time among these waveforms P, QRS, T, and V corresponds to the dilation period W of the ventricle, i.e., a state in which the heart dilates maximally. From the electrocardiogram it follows that in the dilation period W, the motion of the heart is less and this state is comparatively long.

In view of these facts, the collection of radiation image data is performed as follows. First, if the ventricle dilation period W is measured by the measuring unit 12, the controller 10 synchronizing with the measuring unit 12 causes the ray source 4 to emit X-rays 8 to the subject 2. The emission time is, for example, about 0.02 sec. It is desirable that the emission time be less than or equal to 0.1 sec. The reason for this is that if the emission time becomes long, a probability that the heart will move within the time will become high and therefore the image of the outline of the heart will become obscure. Next, either the subject 2 is rotated by 5 degrees with respect to the detector 6 and the ray source 4, or the detector 6 and the ray source 4 are rotated by 5 degrees with respect to the subject 2. Also, as performed initially, emission of the X-rays 8 is performed at the angular position for a predetermined time period in accordance with the dilation period W of the heart. Next, a further rotation of 5 degrees is performed and X-rays 8 are emitted to the subject 2. This operation is repeated so that the emission of X-rays 8 is performed 72 times in one revolution, i.e., a rotation of 360 degrees, and radiation image data are collected.

In the preferred embodiment, although X rays are emitted for the dilation period W of the heart to collect data, other time periods may be employed if they have the same phase as the heartbeats. For example, the T wave, generated when the ventricle contracts, is comparatively long, but in this contraction period Y, motion of the heart is larger compared with the dilation period W and also the time is as short as about 0.1 through 0.15 sec, so the resolution for photographing in this contraction period Y is considered to be slightly lower compared with the dilation period W. It can be understood that the dilation period W of the heart is most suitable for collecting radiation image data. However, it is noted that a time for measurement depends on a point of time that data of heartbeats is needed and is therefore determined each time.

While the present invention has been described with reference to the preferred embodiment thereof, the invention is not to be limited to the details given herein, but may be modified within the scope of the appended claims. For example, although the subject 2 and the radiation tomograph 1 are relatively rotated by a predetermined angle, the angle is not limited to 5 degrees but may be set in various ways.

What is claimed is:

1. A method of radiation tomography for photographing a radiation projected image of a subject by relatively rotating a radiation source which emits a conical radiation beam and a detector which detects said conical radiation beam transmitted through said subject, with respect to said subject, said radiation tomography comprising the steps of:

detecting a periodic motion of a part of said subject to be photographed; and controlling said radiation source so that in synchronism with the detection, a timing of emitting said conical radiation beam is synchronized with constant timing at which the detected part moves; and wherein said radiation source and said detector are rotated with respect to said subject using a plurality of short intervals.

2. The radiation tomography as set forth in claim 1, wherein said detected part is the heart of a living organism and said constant timing is the dilation period of said heart.

3. A radiation tomography apparatus used in photographing a radiation projected image of a subject by relatively rotating a radiation source which emits a conical radiation beam and a detector which detects said conical radiation beam transmitted through said subject, with respect to said subject, said radiation tomography apparatus comprising:

detection means for detecting a periodic motion of a part of said subject to be photographed; and control means for controlling said radiation source so that in synchronism with the detection, a timing of emitting said cone radiation beam is synchronized with constant timing at which the detected part moves; and wherein said radiation source and said detector are rotated with respect to said subject using a plurality of short intervals.

4. The radiation tomography apparatus as set forth in claim 3, wherein said detected part is the heart of a living organism and said constant timing is the dilation period of said heart.

5. The radiation tomography as set forth in the claim 1, wherein said synchronization time for emitting said conical radiation beam toward said subject is done at a time when the movement of said part is at a minimum.

6. The radiation tomography as set forth in claim 3, wherein said synchronization time for emitting said conical radiation beam toward said subject is done at a time when the movement of said part is at a minimum.

7. The radiation tomography as set forth in claim 1, wherein each said short interval is about 5 degrees for emitting said conical radiation beam toward said subject.

8. The radiation tomography apparatus as set forth in claim 3, wherein each said short interval is about 5 degrees for emitting said conical radiation beam toward said subject.

9. The radiation tomography as set forth in claim 5, further comprising the step of emmitting said conical radiation beam toward said subject for up to 0.1 seconds.

10. The radiation tomography as set forth in claim 6, further comprising an emission time of said conical radiation beam is up to 0.1 seconds.

* * * * *